(12) United States Patent
Baratta et al.

(10) Patent No.: US 7,638,628 B2
(45) Date of Patent: Dec. 29, 2009

(54) COMPLEXES OF RUTHENIUM WITH 2-(AMINOMETHYL)PYRIDINES AND PHOSPHINES, THEIR PREPARATION AND USE AS CATALYSTS

(75) Inventors: Walter Baratta, Udine (IT); Katia Siega, Tarvisio (IT); Micaela Toniutti, Udine (IT); Pierluigi Rigo, Udine (IT)

(73) Assignee: Universita' Degli Studi Di Udine, Udine (IT)

( * ) Notice: Subject to any disclaimer, the term of this patent is extended or adjusted under 35 U.S.C. 154(b) by 447 days.

(21) Appl. No.: 11/579,371

(22) PCT Filed: May 2, 2005

(86) PCT No.: PCT/EP2005/051998

§ 371 (c)(1),
(2), (4) Date: Nov. 2, 2006

(87) PCT Pub. No.: WO2005/105819

PCT Pub. Date: Nov. 10, 2005

(65) Prior Publication Data

US 2008/0249308 A1    Oct. 9, 2008

(30) Foreign Application Priority Data

May 4, 2004    (IT)    ............... PD04A0115

(51) Int. Cl.
*C07F 15/00*    (2006.01)
*B01J 31/12*    (2006.01)
(52) U.S. Cl. .......................................... 546/2; 502/167
(58) Field of Classification Search ............ 546/2; 502/167
See application file for complete search history.

(56) References Cited

U.S. PATENT DOCUMENTS

| | | | |
|---|---|---|---|
| 6,184,381 B1 | 2/2001 | Ikariya et al. | |
| 6,372,931 B1 | 4/2002 | Blacker et al. | |
| 6,451,727 B2 | 9/2002 | Zhang | |
| 6,545,188 B2 | 4/2003 | Blacker et al. | |

FOREIGN PATENT DOCUMENTS

JP    11-189600    7/1999

OTHER PUBLICATIONS

Baratta, Walter et al., "RuCl$_2$ [(2,6-Me$_2$C$_6$H$_3$) PPh$_2$]$_2$: A New Precursor for Cylometalated . . . ", Organometallics 2004, pp. 6264-6272.
Thoumazet, Claire et al., "A Cationic 1-(2-Methylpyridine)Phosphole Cymene . . . ", Organometallics 2003, pp. 1580-1581.
International Search Report Written Opinion of the International Searching Authority.

Noyori, R., "Asymmetric Catalysis in Organic Synthesis", Department of Chemistry, 1994, pp. 56-82. (Spec, p. 1).
Ohkuma, T. et al., "Preferential Hydrogenation of Aldehydes and Ketones ", J. Am. Chem. Soc. 1995, vol. 117, pp. 10417-10418. (Spec, p. 1).
Noyori, R. et al., "Asymmetric Catalysis by Architectural and Functional Molecular Engineering: Practical Chemo- and Stereoselective Hydrogenation of Ketones", Angew. Chem., Int. Ed. Engl. 2001, vol. 40, pp. 40-73. (Spec, p. 1).
Crépy, K. V. L. et al., "Recent Developments in Catalytic Asymmetric Hydrogenation Employing P-Chirogenic Diphosphine Ligands", Adv. Synth. Catal. 2003, vol. 345, pp. 79-101. (Spec, p. 1).
Zassinovich, G. et al., "Asymmetric Hydrogen Transfer Reactions Promoted by Homogeneous Transition Metal Catalysts", Chem. Rev. 1992, vol. 92, pp. 1051-1069. (Spec, pp. 1-2).
Noyori, R. et al., "Asymmetric Transfer Hydrogenation Catalyzed by Chiral Ruthenium Complexes", Acc. Chem. Res. 1997, vol. 30, pp. 97-102. (Spec, p. 2).
Bäckvall, J.-E., "Transition metal hydrides as active intermediates in hydrogen transfer reactions", J. Organomet. Chem. 2002, vol. 652, pp. 105-111. (Spec, p. 2).
Palmer, M. J. et al., "Asymmetric transfer hydrogenation of C=O and C=N bonds", Tetrahedron: Asymmetry 1999, vol. 10, pp. 2045-2061. (Spec, p. 2).
Hiller, A. C. et al., "Cationic Iridium Complexes Bearing Imidazol-2-ylidene Ligands as Transfer Hydrogenation Catalysts", Organometallics 2002, vol. 20, pp. 4246-4252. (Spec, p. 2).
Gao, J.-X. et al., "A Ruthenium (II) Complex with a C$_2$-Symmetric . . . ", Organometallics, 1996, vol. 15, pp. 1087-1089. (Spec, p. 2).
Haack, K.-J. et al., "The Catalyst Precursor, Catalyst, and Intermediate in . . . ", Angew. Chem., Int. Ed. Engl. 1997, vol. 36, pp. 285-288. (Spec, p. 2).
Everaere, K. et al., "Ruthenium (II)-Catalyzed Asymmetric Transfer Hydrogenation of Carbonyl Compounds with 2-Propanol and Ephedrine-Type Ligands", Adv. Synth. Catal. 2003, vol. 345, pp. 67-77. (Spec, p. 2).
Jiang, Y. et al., "A New Chiral Bis(oxazolinylmethyl)amine Ligand for Ru-Catalyzed Asymmetric Transfer Hydrogenation of Ketones", J. Am. Chem. Soc. 1998, vol. 120, pp. 3817-3819. (Spec, p. 2).

(Continued)

*Primary Examiner*—Charanjit S Aulakh
(74) *Attorney, Agent, or Firm*—Collard & Roe, P.C.

(57) ABSTRACT

The invention relates to a new class of ruthenium (II) complexes containing as ligands 2-(aminomethyl)pyridines and phosphines, proven to be extremely active catalysts in the reduction of ketones to alcohols via hydrogen transfer. By using 2-propanol as the hydrogen source with the ruthenium complexes, high yields of the corresponding alcohol can be rapidly obtained starting from linear and cyclic alkyl aryl, dialkyl and diaryl ketones. The conversion of ketones to alcohols can reach 100% if operating in a gaseous hydrogen atmosphere (2-3 atm). Where the phosphines used are optically active, starting from prochiral ketone compounds various types of optically active alcohols can be produced, being important intermediates in the pharmaceutical industry, in the agrochemical industry and for fine chemicals generally.

15 Claims, No Drawings

OTHER PUBLICATIONS

Nishibayashi, Y. et al., "Extremely High Enantioselective Redox Reaction of Ketones and Alcohols Catalyzed by . . . ", Organometallics 1999, vol. 18, pp. 2291-2293. (Spec, p. 2).

Dani, P. et al., "Hydrogen-Transfer Catalysis with Pincer-Aryl Ruthenium(II) Complexes", Angew. Chem., Int. Ed. Engl. 2000, vol. 39, pp. 743-745. (Spec, pp. 3 and 19).

Yang, H. et al., "Ruthenium(II) Complexes with New Tridentate Ligands containing P, N, O Donor Atoms: Highly Efficient Catalysts for Transfer Hydrogenation of Ketones by Propan-2-ol", J. Chem. Soc., Chem. Commun. 1995, pp. 1721-1772. (Spec, p. 3).

Yang, H. et al., "Ruthenium (II) Complexes Containing Optically Active Hemilabile P, N, O-Tridentate Ligands . . . ", Organometallics, 1997, vol. 16, pp. 1401-1409. (Spec, p. 3).

Thoumazet, C. et al., "A Cationic 1-(2-Methylpyridine) Phosphole Cymene Ruthenium Chloride Complex as an Efficient Catalyst in the Transfer Hydrogenation of Ketones", Organometallics, 2003, vol. 22, pp. 1580-1581. (Spec, p. 3).

Mizushima, E., "Asymmetric transfer hydrogenation of aryl-alkyl ketones catalyzed by ruthenium(II) complexes having chiral pyriylmethylamine and phosphine ligands", J. Mol. Catal. A 1999, vol. 149, pp. 43-49. (Spec, p. 3).

Brunner, H. et al., "Enantioselective Catalysis CXLI [1]. Tridentate Ligands with . . . ", Monatshefte für Chemie 2002, vol. 133, pp. 115-126. (Spec, p. 3).

Brunner, H. et al., "Enantioselective catalysis. Part 143: Astonishingly high enantioselectivity in the transfer hydrogenation of . . . ", Tetrahedron: Asymmetry 2002, vol. 13, pp. 37-42. (Spec, p. 3).

COMPLEXES OF RUTHENIUM WITH 2-(AMINOMETHYL)PYRIDINES AND PHOSPHINES, THEIR PREPARATION AND USE AS CATALYSTS

CROSS REFERENCE TO RELATED APPLICATIONS

Applicants claim priority under 35 U.S.C. §119 of Italian Application No. PD2004A000115 filed May 4, 2004. Applicants also claim priority under 35 U.S.C. §365 of PCT/EP2005/051998 filed May 2, 2005. The international application under PCT article 21(2) was published in English.

FIELD OF THE INVENTION

The invention relates to a class of ruthenium(II) complexes containing 2-(aminomethyl)pyridines and phosphines, being chiral in some cases, and to their use as catalysts in the reduction of ketones to alcohols by means of hydrogen transfer. The rate of reduction and the alcohol yield can be further increased by operating in the presence of low pressure (2-3 atmospheres) molecular hydrogen.

STATE OF THE ART

The reduction of carbonyl compounds to alcohols is a reaction of wide-ranging applicative interest and over recent years this has led to the development of a series of catalytic methods intended to substitute the classical stoichiometric reduction systems. Good results have been obtained for reduction with molecular hydrogen using catalytic systems based on transition metals (Ir, Rh, Pd, Ni), but in particular, attention has lately been concentrated on the more active ruthenium derivatives. Compounds of the type [RuCl$_2$ (phosphine)$_2$(1,2-diamine)] and [RuCl$_2$(diphosphine)(1,2-diamine)] in a basic environment are excellent catalysts for the selective hydrogenation, in homogeneous phase, of varying types of ketones. In addition, with a suitable combination of chiral diphosphines and diamines, enantioselective hydrogenation of carbonyl compounds can be achieved with the formation of optically active alcohols with enantiomeric excesses of nearly 100%. The reactions are generally conducted with hydrogen under pressure at moderate temperatures (R. Noyori, *Asymmetric Catalysis in Organic Synthesis*, Ed. R. Noyori, 1994, pp. 56-82; T. Ohkuma, H. Ooka, T. Ikariya, R. Noyori, *J. Am. Chem. Soc.* 1995, 117, 10417; R. Noyor, T. Ohkuma, *Angew. Chem., Int. Ed. Engl.* 2001, 40, 40; K. V. L. Crépy, T. Imamoto, *Adv. Synth. Catal.* 2003, 345, 79). As an alternative to reduction processes with molecular hydrogen, which is a possible source of risk, catalytic reduction methods based on hydrogen transfer reactions have also been established. In these processes 2-propanol is normally used as hydrogen source and reaction solvent, with the advantage of being a low boiling point liquid and having low toxicity and low environmental impact (G. Zassinovich, G. Mestroni, S. Gladiall, *Chem. Rev.* 1992, 92, 1051; R. Noyod, S. Hashiguchi, *Acc. Chem. Res.* 1997, 30, 97; J.-E. Bäclkvall, *J. Organomet Chem.* 2002, 652, 105; M. J. Palmer, M. Wills, *Tetrahedron: Asymmetry* 1999, 10, 2045). Due to its simplicity of operation and due to the good results that it can give, catalytic transfer of hydrogen is a useful alternative to reduction with molecular hydrogen primarily for small and medium scale reactions. Transition metal based catalysts such as rhodium and iridium have been used (M. J. Palmer, M. Wills, 1999 ref. cit; A. J. Blazer, B. J. Mellor, U.S. Pat. No. 6,372,931, 2002 and U.S. Pat. No. 6,545,188, 2003; A. C. Hillier, H. M. Lee, E D. Stevens, S. P, Nolan, *Organometallics* 2001, 20, 4246) but the most interesting results, in particular for the enantioselective reduction of ketones, have been achieved with ruthenium derivatives. Among which: complexes with tetradentate ligands of diphosphine-diamine and diphosphine-dilmine type (J.-X. Gao, T. Ikarya, R. Noyori, *Organometallics,* 1996, 15, 1087), arene-ruthenium complexes with diamine or β-aminoalcohol ligands (K.-J. Haack, S. Hashiguchi, A. Fujii, T. Ikardya, R. Noyod, *Angew. Chem. Int Ed. Engl.* 1997, 36, 285; T. Ikariya S. Hashiguchi, J. Takehara, N. Uematsu, K. Matsumara, R. Noyori, A. Fujii, U.S. Pat. No. 6,184,381, 2001; K Everaere, A. Mortreaux, J. Carpentier, *Adv. Synth. Catal.* 2003, 345, 67), complexes with oxazoline ligands (Y Jiang, Q. Jiang, X, Zhang, *J. Am. Chem. Soc.* 1998, 120, 3817; X. Zhang, U.S. Pat. No. 6,451,727, 2002), with oxazolinylferrocenylphosphine ligands (Y. Nishibayashi, I. Takei, S. Uemura, M. Hidal, *Organometallics* 1999, 18, 2291). In this way, by using chiral ligands, optically active alcohols, which have important applications in the pharmaceutical field, in agrochemistry and for fine chemicals generally, can be easily prepared. Generally the reactions are conducted in the presence of strong bases such as alkali metal hydroxides or alkoxides, with substrate/catalyst ratios between 20 and 2000, with fairly high % conversion of starting ketone to alcohol, and with enantioselectivity up to 99%. It should be noted that these catalytic systems do not in general have a high activity and that they present TOF values (turnover frequency=number of moles of ketone converted to alcohol per mole of catalyst per hour at 50% conversion) in general of between $10^2$ and $10^3$ h$^{-1}$. This entails long reaction times and low plant utilization in addition to the risk of the catalyst deactivation and decomposition over time, which can greatly affect product cost. To be noted are the particularly active catalytic systems for non enantioselective reduction of ketones obtained by van Koten and collaborators (P. Dani, T. Karien, R. A. Gossage, S. Gladiali, G. van Koten; *Angew. Chem., Int Ed. Engl.* 2000, 39, 743) of pincer-aryl type of formula RuX[C$_6$H$_3$(CH$_2$FPh$_2$)$_2$-2,6](PPh$_3$) (X=Cl, CF$_3$SO$_3$), having a stable Ru—C aryl bond, and those published by Mathieu containing tridentate pyridine ligands, which exhibit TOF values of up, to 90000 h$^{-1}$ for the acetophenone reduction (H. Yang, M. Alvarez, N. Lugan, R. Mathieu, *J. Chem. Soc., Chem. Commun.* 1995, 1721; H. Yang, M. Alvarez-Gressier, N. Lugan, R. Mathieu, *Organometallics* 1997, 16, 1401) even if their rapid deactivation limits their use in organic synthesis. Moreover, in a recent study, Mathey and Le Floch (C. Thoumazet, M. Melaimi, L. Ricard, F. Mathey, P. Le Floch, *Organometallics* 2003, 22, 2580) described a new arene ruthenium catalyst containing the ligand N, P bidentate 1-(2-methylpyridine)-2,5 diphenyl phosphole, which exhibits TOF values of up to 10$^6$ h$^{-1}$ for numerous ketones, but the extremely long periods of time (several days at 90° C.) limit its practical use. It has also been reported that ruthenium complexes of general formula RuXY (PR$_1$R$_2$R$_3$)$_n$(NR$_6$R$_7$R$_8$)$_m$ [X and Y=H or halogen atom; R$_1$—R$_3$=hydrocarbon possibly substituted e.g. a phenyl; R$_6$-R$_8$=H or substituted hydrocarbon atom and n and m=04] can act as catalysts in hydrogen transfer or hydrogenation reactions (T. Ikariya, H. Ikehira, K. Murata, N. Kiyofuji, H. Oooka, S. Hashiguchi, T. Okuma, R. Noyori Japanese Patent, 11189600). To be also noted is that chiral 2-(aminomethyl) pyridines mono substituted at the nitrogen have been used, in association with the precursor RuCl$_2$(PPh$_3$)$_3$, to obtain in situ catalytic systems for enantioselective hydrogen transfer reactions. These systems have a somewhat low activity with from moderate enantioselectivity (E. Mizushima, H. Ohi, M. Yamaguchi, T Yamagishi, *J. Mol. Catal. A* 1999, 149, 43) to good enantioselectivity (H. Brunner, M. Niemetz, *Monatshefte für Chemie* 2002, 133, 115; H. Brunner, F. Henning, M. Weber, *Tetrahedron: Asymmetry* 2002, 13, 37). In order to render the reduction of ketones to alcohols by hydrogen transfer economically competitive, the primary aim is therefore to develop catalysts with greater activity and productivity than those previously described. This is particularly important if the catalytic systems can lead to enantioselective reduction reactions, allowing their use for synthesising optically active alcohols from prochiral ketones.

One purpose of the present invention is therefore to obtain ruthenium complexes which can be used as highly active catalysts in the asymmetric and non-asymmetric reduction of ketones by hydrogen transfer. A further purpose of the present invention is to obtain ruthenium(II) complexes which can be employed as catalysts generated in situ during the asymmetric and non-asymmetric reduction of ketones by hydrogen transfer.

SUMMARY

To attain the aforementioned purposes, the inventors have identified, in a new class of ruthenium(II) complexes with 2-(aminomethyl)pyridine ligands, the solution for obtaining catalysts with very high catalytic activity, with the possibility of also achieving enantioselective catalysis by suitable combination with chiral phosphines. The catalysts are also obtainable with in situ synthesis processes. It should be emphasised that the systems here described function as catalysts for ketone hydrogenation with molecular hydrogen under low pressure and ambient temperature conditions.

The invention therefore provides ruthenium(II) complexes of general formula (I)

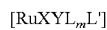

in which
X, Y, L, L' can be:
X, Y equal or different and be a halogen or a hydrogen
L ligands chosen from the groups comprising:
a) a monodentate phosphine of general formula $PR^1R^2R^3$ where $R^1$, $R^2$ and $R^3$ can be equal or different and can be aliphatic or aromatic groups;
b) a bidentate phosphine of the of general formula $PR'_2(CH_2)_x PR''_2$ with x equal to 2, 3 or 4 where R' and R'' can be equal or different and be aliphatic or aromatic groups;
c) an optically active diphosphine;

and m can be equal to 1 or 2 with the proviso that m is equal to 1 when the ligand L is chosen from group b) or c) and equal to 2 when the ligand L is chosen from group a) and that in this case the ligands L can be equal or different;

L' a bidentate ligand of 2-(aminomethyl)pyridine type of formula (II)

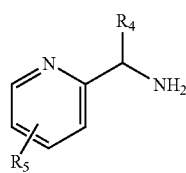

where $R^4$, $R^5$ can be equal or different and can be H, aliphatic or aromatic groups. Further aspects of the invention are the synthesis processes, also in situ, of the ruthenium(II) complexes of the invention, and the ruthenium(II) complexes directly obtained in situ with said processes during the reduction of ketones by transferring hydrogen from an alcohol to said ketones.

Further aspects of the invention are the use of said ruthenium(II) complexes as catalysts for the reduction of ketones by hydrogen transfer.

Further aspects of the invention are the use of said ruthenium(II) complexes as catalysts for the reduction of ketones by reaction with gaseous hydrogen.

Reduction by transferring hydrogen from an alcohol and reduction with gaseous hydrogen can be combined thus resulting in the complete conversion of ketone to alcohol.

These and other aspects, as well as the characteristics and advantages of the present invention, will be more apparent from the detailed description below and by the preferred embodiments given as non-limiting illustrations of the invention itself.

DETAILED DESCRIPTION OF THE INVENTION

As previously mentioned, ruthenium complexes of general formula $RuXY(PR_1R_2R_3)_n(NR_6R_7R_8)_m$, in which X and Y can be a halogen or a hydrogen, $(PR_1R_2R_3)$, can be a ligand of the monodentate (n=2) or bidentate (n=1) phosphine type and $(NR_6R_7R_8)_m$ can be a diamine, have been used as catalysts in hydrogen transfer or hydrogenation reactions (T. Ikariya et al ref. cit.). Also, catalytic systems, which are generated in situ from chiral pyridine ligands of 2-(RHN—CHR)C$_5$H$_4$N type combined with the precursor $RuCl_2(PPh_3)_3$, have been found to be active in enantioselective hydrogen transfer reactions. It should be emphasised however that in the first case 2-(aminomethyl)pyridines are not included among the bidentate nitrogen ligands mentioned, the former being ligands essential to the aims of the present invention, and in the second case the chiral pyridines used of 2-(RHN—CHR)C$_5$H$_4$N type give systems which result in somewhat low activity with from moderate enantioselectivity (E. Mizushima, et al ref. cit.) to good enantioselectivity (H. Brunner et al. ref cit.). The previously mentioned results have not therefore shown that the bidentate ligands of 2-(aminomethyl)pyridine type, in combination with monodentate or bidentate phosphine, can be used to obtain ruthenium complexes which are particularly active as catalysts in hydrogen transfer reactions. Also to be emphasised is the greater catalytic activity, not previously highlighted, of the dichloro derivatives (X=Y=Cl) in which the chlorine atoms are in cis orientation.

The new ruthenium(II) complexes of the present invention, usefully employable in reactions for reducing ketones to alcohols, possibly chiral, by hydrogen transfer are represented by the general formula (I)

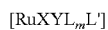

in which
X, Y, L, L' can be:
X, Y equal or different and are a halogen or a hydrogen
L ligands chosen from the groups comprising:
a) a monodentate phosphine of general formula $PR^1R^2R^3$ where $R^1$, $R^2$ and $R^3$ can be equal or different and are aliphatic or aromatic groups;
b) a bidentate phosphine of $PR'_2(CH_2)_x PR''_2$ type, x=2, 3, 4 where R' and R'' can be equal or different and are aliphatic or aromatic groups;
c) an optically active diphosphine;

with m equal to 2 in the case of equal or different monodentate phosphines chosen from group a) and equal to 1 if the phosphine is chosen from group b) or c);

L' a bidentate ligand of 2-(aminomethyl)pyridine type of formula (II)

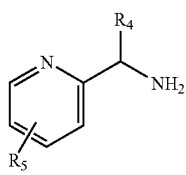

(II)

where $R^4$, $R^5$ can be equal or different and are H, aliphatic or aromatic groups. The complexes can present the two ligands X and Y in trans or cis orientation. By way of example the structures of two of the possible cis and trans isomers, where $R^4=R^5=H$, are given in the FIGURE:

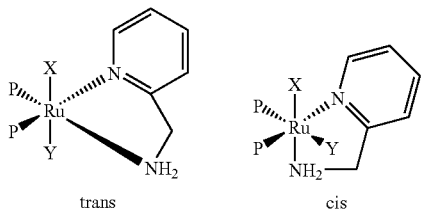

For the purposes of the present invention, ruthenium(II) complexes with the general formulas given below are obtained from combinations of the various meanings for X, Y, L, L' and m,:

trans or cis ruthenium(II) complexes of formula (III)

trans or cis-[RuXYL₂L']    (III)

in which X, Y independently are a halogen or a hydrogen,
L are monodentate phosphines, equal or different, chosen from group a),
L' is a bidentate ligand of 2-(aminomethyl)pyridine type of formula (II);

trans or cis ruthenium(II) complexes of formula (IV)

trans or cis [RuXYL₁L']    (IV)

in which X, Y independently are a halogen or hydrogen,
L is a bidentate phosphine chosen from group b) or an optically active diphosphine chosen from group c),
L' is a bidentate ligand of 2-(aminomethyl)pyridine type of formula (II).

For the purposes of the present invention the preferred X and Y ligands are: chlorine and hydrogen; the preferred L ligands of group a) are PPh₃; of group b) are: PPh₂(CH₂)₂PPh₂, PPh₂(CH₂)₃PPh₂, PPh₂(CH₂)₄PPh₂; of group c) are: (2S,3S)-(−)-2,3-bis-(diphenylphosphino)butane (CHIRAPHOS), (S)-(−)-2,2'-bis-(di-p-tolylphosphino)-1,1'-binaphthyl (Tol-BINAP), (2S,4S)-(−)-2,4-bis-(diphenylphosphino) pentane (SKEWPHOS), (4R,5R)-(−)-O-isopropylidene-2,3-dihydroxo-1,4-bis(diphenylphosphino)butane (DIOP), (R)-(−)-1[(S)-2-(diphenylphosphino)ferrocenyl] ethyldicyclohexylphosphine (JOSIPHOS), whereas the preferred meaning of $R^4$ ed $R^5$ of the ligand L' of formula (II) is H and therefore the preferred ligand L' is 2-(aminomethyl) pyridine.

Specific examples of complexes which have been isolated and used in catalysis by way of non-limiting examples of the present invention are given below.

1. Ruthenium complexes of general formula (III)

trans-[RuXYL₂L']    (III)

where L' is 2-(aminomethyl)pyridine, L is PPh₃ and X=Y=Cl (3) or X=H and Y=Cl (4)

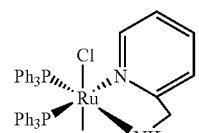

(3)

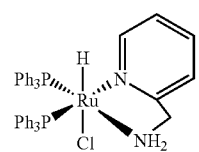

(4)

2. Ruthenium complexes of general formula (III)

cis-[RuXYL₂L']    (III)

where L' is 2-(aminomethyl)pyridine, L is PPh₃ and X=Y=Cl (5) or X=Y=H (6).

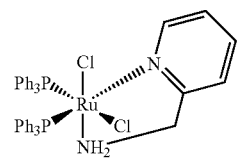

(5)

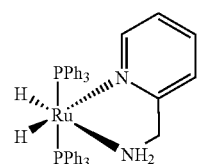

(6)

3. Ruthenium complexes of general formula (IV)

trans-[RuXYLL']    (IV)

where L' is 2-(aminomethyl)pyridine, L is PPh₂(CH₂)₄PPh₂ and X=Y Cl (7).

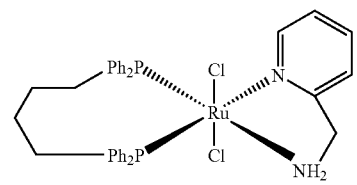

(7)

4. Ruthenium complexes of general formula (IV)

cis-[RuXYLL']    (IV)

where L' is 2-(aminomethyl)pyridine, X=Y=Cl and L is one of the diphosphines PPh$_2$(CH$_2$)$_2$PPh$_2$ (8), PPh$_2$(CH$_2$)$_3$PPh$_2$ (9), and PPh$_2$(CH$_2$)$_4$PPh$_2$ (10).

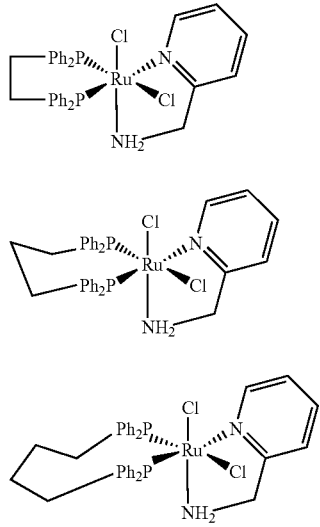

(8)

(9)

(10)

or where L is a chiral diphosphine such as (2S,3S)-(−)-2,3-bis-(diphenylphosphino)butane (CHIRAPHOS) (11), (2S,4S)-(−)-2,4-bis-(diphenylphosphino)pentane (SKEWPHOS) (12), (4R,5R)-(−)-O-isopropylidene-2,3-dihydroxy-1,4-bis(diphenylphosphino)butane (DIOP) (13), (R)-(−)-1-[(S)-2-(diphenylphosphino)ferrocenyl]ethyldicyclohexylphosphine (JOSIPHOS) (14), (S)-(−)-2,2'-bis-(di-p-tolylphosphino)-1,1'-binaphthyl (Tol-BINAP) (15),

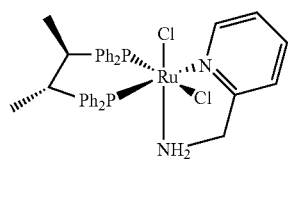

(11)

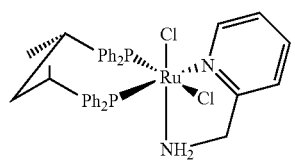

(12)

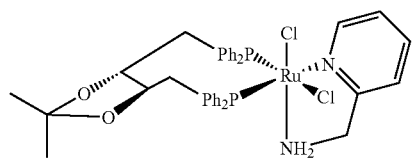

(13)

-continued

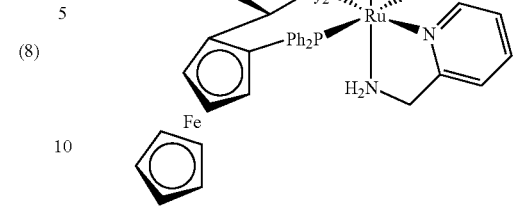

(14)

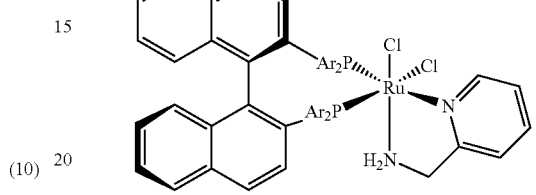

(15)

Ar = 4-MeC$_6$H4

A. Synthesis of Ruthenium Complexes

Synthesis of the complexes (3-15) of the invention uses the compound RuCl$_2$(PPh$_3$)$_3$ (1) as starting product

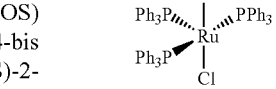

(1)

which is commercially available or can be prepared by reacting hydrated RuCl$_3$ with triphenylphosphine (R. Holm, *Inorg. Synth.* 1970, 12, 238), while the complex RuCl$_2$(PPh$_2$(CH$_2$)$_4$PPh$_2$)(PPh$_3$) (2)

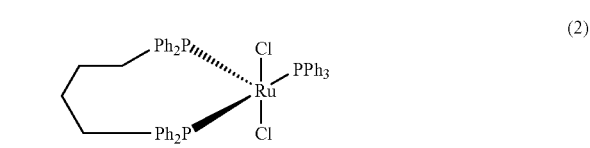

(2)

was prepared in accordance with the procedure published in the literature (C. W Jung, P. E. Garrou, P. R. Hoffnan, K. G. Caulton, *Inorg. Chem.* 1984, 23, 726). The complex (3) of trans geometry is obtained by reacting RuCl$_2$(PPh$_3$)$_3$ (1) in dichloromethane at ambient temperature with 2-(aminomethyl)pyridine in a 1:1 ratio, while the cis complex (5) is prepared by reacting RuCl$_2$(PPh$_3$)$_3$ (1) with 2-(aminomethyl)pyridine in toluene under reflux. By following the procedure of (3), starting from (2) and reacting with 2-(aminomethyl)pyridine, the trans derivative (7) is obtained. The catalysts (8-13) of cis geometry are prepared starting from complex (5) and reacting in a 1:1 ratio with a suitable diphosphine. The catalysts (14) and (15) are synthesised from (1) with a suitable chiral diphosphine and subsequent addition of 2-(aminomethyl)pyridine. For the complex (10) two other more rapid synthesis paths are also given starting from (2) with the amine (method a) or starting from (1) with the amine and the corresponding diphosphine (method b). The monohydride complex (4) was prepared starting from the 2-(aminomethyl)pyridine and RuHCl(PPh$_3$)$_3$ synthesised from (1) (R. A. Schunn, E. R. Wonchoba, *Inorg. Synth.* 1971, 13, 131) while the dihydride complex (6) was obtained from (4) by reacting with sodium isopropoxide.

As non-limiting examples of the present invention the syntheses and the characteristics of the complexes (3)-(6), (10), (12), and (14) are described in detail. All the syntheses were carried out under argon atmosphere, using distilled or previously de-aerated solvents.

EXAMPLE 1

Synthesis of the complex trans-RuCl$_2$(PPh$_3$)$_2$[2-(H$_2$NCH$_2$)C$_5$H$_4$N](3)

The complex RuCl$_2$(PPh$_3$)$_3$ (1) (0.400 g, 0.417 mmol), suspended in 5 ml of distilled dichloromethane, is reacted with 2-(aminomethyl)pyridine (45 μL, 0.436 mmol). After leaving the mixture under stirring for 2 hours at ambient temperature, the volume of the solution is reduced to about one half and the complex is precipitated by adding 5 ml of pentane. The solid obtained is filtered off, washed twice with 10 ml of ethyl ether and dried under reduced pressure.

Yield 250 mg (75%). Elemental analysis (%) calculated for C$_{42}$H$_{38}$Cl$_2$N$_2$P$_2$Ru. C, 62.69; H, 4.76; N, 3.48; found C, 62.85; H, 4.80; N, 3.54. $^1$H NMR (200.1 MHz, CDCl$_3$, 20° C., TMS): δ 8.53 (d, J(HH)=4.2 Hz, 1H; o-C$_5$H$_4$N), 7.60-6.50 (m, 33H; aromatic protons), 4.46 (wide-s, 2H; CH$_2$), 3.29 (wide s, 2H; NH$_2$). $^{13}$C{$^1$H} NMR (50.3 MHz, CDCl$_3$, 20° C., TMS): δ 162.8 (s; NCCH$_2$), 157.6 (s; NCH of C$_5$H$_4$N), 136.6-120.1 (m; aromatic C), 50.8 (s; CH$_2$). $^{31}$P{$^1$H} NMR (81.0 MHz, CDCl$_3$, 20° C., H$_3$PO$_4$): 844.0 (d, J(PP)=32.7 Hz), 40.1 (d, J(PP)=32.7 Hz).

EXAMPLE 2

Synthesis of the complex trans-RuHCl(PPh$_3$)$_2$[2-(H$_2$NCH$_2$)C$_5$H$_4$N](4)

The complex RuHCl(PPh$_3$)$_3$ (211 mg, 0.228 mmol), suspended in 10 ml of heptane, is reacted with 2-(aminomethyl)pyridine (24 μL, 0.233 mmol) and refluxed for 1 hour. The yellow product is filtered off, washed with heptane (3×5 ml) and dried under reduced pressure.

Yield: 118-mg (67%). Elemental analysis (%) calculated for C$_{42}$H$_{39}$ClN$_2$P$_2$Ru: C, 65.49; H, 5.10; N, 3.64; found: C, 65.23; H, 5.03; N, 3.41. $^1$H NMR 200.1 MHz, CD$_2$Cl$_2$, 20° C., TMS): δ 8.20 (s, 1H; o-C$_5$H$_4$N), 7.70-6.40 (m, 33H; aromatic protons), 4.30 (pseudo t, J(HH)=14.1 Hz, 1H; CH$_2$), 4.07 (d, J(HH)=14.3 Hz, 1H; CH$_2$), 2.87 (pseudo t, J(HH)=10 Hz, 1H; NH$_2$), 2.20 (pseudo d, J(HH)=10 Hz, 1H; NH$_2$), -17.70 (dd, J(HP)=23.5, 29.7 Hz). $^{13}$C{$^1$H} NMR (50.3 MHz, CD$_2$Cl$_2$, 20° C., TMS): δ 159.7 (s; NCCH$_2$), 155.6 (d, J(CP)=4.0 Hz; NCH), 138.8-118.7 (m; aromatic C), 53.4 (s; CH$_2$). $^{31}$P{$^1$H} NMR (81.0 MHz, CD$_2$Cl$_2$, 20° C., H$_3$PO$_4$): δ 73.7 (d, J(PP)=37.0 Hz), 68.9 (d, J(PP)=37.0 Hz).

EXAMPLE 3

Synthesis of the complex cis-RuCl$_2$(PPh$_3$)$_2$[2-(H$_2$NCH$_2$)C$_5$H$_4$N](5)

The complex RuCl$_2$(PPh$_3$)$_3$ (1) (1.34 g, 1.40 mmol), suspended in 10 ml of toluene, is reacted with 2-(aminomethyl)pyridine (0.160 ml, 1.55 mmol). The mixture is refluxed for 2 hours; the solution volume is then reduced to one half and the complex is precipitated by adding 5 ml of pentane. The solid obtained is filtered off, washed twice with 5 ml of ethyl ether and dried under reduced pressure.

Yield: 750 mg (66.4%). Elemental analysis (%) calculated for C$_{42}$H$_{38}$Cl$_2$N$_2$P$_2$Ru: C, 62.69; H, 4.76; N, 3.48; found: C, 62.31; H, 4.87; N, 3.60. $^1$H NMR (200.1 MHz, CD$_2$Cl$_2$, 20° C., TMS): δ 9.16 (d, J(HH)=5.7 Hz, 1H; ortho-C$_5$H$_4$N), 7.70-6.89 (m, 33H; aromatic protons), 3.65 (m, 2H; CHHNHH), 3.00 (m, 1H, CH$_2$), 1.42 (m, 1H, NH$_2$). $^{31}$P{$^1$H} NMR (81.0 MHz, CD$_2$Cl$_2$, 20° C., H$_3$PO$_4$): δ 50.5 (d, J(PP)=33.4 Hz), 43.8 (d, J(PP)=33.4 Hz).

EXAMPLE 4

Synthesis of the complex cis-RuH$_2$(PPh$_3$)$_2$[2-(H$_2$NCH$_2$)C$_5$H$_4$N](6)

1.4 ml of a sodium isopropoxide solution in 2-propanol (0.2 M; 0.280 mmol) are placed in a Schlenk and the solvent is evaporated under reduced pressure. By adding the complex (4) (211 mg, 0.274 mmol) and toluene (12 ml) a suspension is obtained which is maintained at 30° C. for 3 hours and filtered. By evaporating the toluene under reduced pressure a dark red solid is obtained which is dried under reduced pressure.

Yield: 131 mg (65%). Elemental analysis (%) calculated for C$_{42}$H$_{40}$N$_2$P$_2$Ru: C, 68.56; H, 5.48; N, 3.81; found: C, 68.30; H, 5.33; N, 3.62. $^1$H NMR (200.1 MHz, C$_6$D$_6$, 20° C., TMS): δ 7.93-5.73 (m, 34H; aromatic protons), 2.76 (t, J(HH)= 6.2 Hz, 2H; CH$_2$), 1.67 (t, J(HH)=6.0 Hz, 2H; NH$_2$), -16.31 (td, J(HP)=27.5 Hz, J(HH)=6.7 Hz, 1H; RuH), -18.24 (td, J(HP)=27.7 Hz, J(HH)=6.7 Hz, 1H; RuH). $^{13}$C{$^1$H} NMR (50.3 MHz, C$_6$D$_6$, 20° C., TMS): 8158.7 (s; NCCH$_2$), 155.8 (s; NCH), 142.0-118.0 (m; aromatic C), 51.4 (s; CH$_2$). $^{31}$P{$^1$H} NMR (81.0 MHz, C$_6$D$_6$, 20° C., H$_3$PO$_4$): δ 67.2.

EXAMPLE 5

Synthesis of the complex cis-RuCl$_2$[PPh$_2$(CH$_2$)$_4$PPh$_2$][2-(H$_2$NCH$_2$)C$_5$H$_4$N] (10) (Method a)

The complex RuCl$_2$-[PPh$_2$(CH$_2$)$_4$PPh$_2$](PPh$_3$) (2) (202 mg, 0.235 mmol), suspended in 5 ml of toluene, is reacted with 2-(aminomethyl)pyridine (27 μL, 0.262 mmol) and the mixture is refluxed for 20 hours. The product obtained on addition of pentane is filtered off, washed twice with 3 ml of ethyl ether and dried under reduced pressure.

Yield: 126 mg (76%). Elemental analysis (%) calculated for C$_{34}$H$_{36}$Cl$_2$N$_2$P$_2$Ru: C, 57.79; H, 5.14; N, 3.96; found: C, 57.48; H, 5.27; N, 3.70. $^1$H-NMR (200.1 MHz, CDCl$_3$, 20° C., TMS): δ 9.36 (m, 1H; ortho-C$_4$H$_5$N), 8.23-6.62 (m, 23H; aromatic protons), 4.13 (m, 1H; CHHP), 3.74 (m, 2H; CHHN, NHH), 3.22 (m, 1H, CHHN), 2.82 (m, 1H, CHHP), 2.34-0.90 (m, 7H; P(CH$_2$)$_4$P, NHH. $^{13}$C{$^1$H} NMR (50.3 MHz, CDCl$_3$, 20° C., TMS): δ 158.0 (s; NCCH$_2$), 151.1 (s; NCH), 136.5-119.8 (m; aromatic C), 53.5 (s; CH$_2$N), 34.8 (d, J(CP)=27.0 Hz; CH$_2$P), 29.7 (d, J-(C,P)=29.9 Hz; CH$_2$P), 27.6 (s; CH$_2$), 19.7 (s; CH$_2$). $^{31}$P{$^1$H} NMR (81.0 MHz, CDCl$_{31}$ 20° C., H$_3$PO$_4$): δ 54.9 (d; J(PP)=37.0 Hz), 40.1 (d; J(PP)=37.0 Hz).

EXAMPLE 6

Synthesis of the complex cis-RuCl$_2$[PPh$_2$(CH$_2$)$_4$PPh$_2$][2-(H$_2$NCH$_2$)C$_5$H$_4$N] (10) (Method b)

The complex RuCl$_2$(PPh$_3$)$_3$ (1) (1.95 g, 2.03 mmol), suspended in 30, ml of toluene, is reacted with 2-(aminomethyl)

pyridine (0.250 mL, 2.43 mmol) under reflux for 1 hour at 110° C. The phosphine PPh$_2$(CH$_2$)$_4$PPh$_2$ (853 mg, 2.00 mmol) is added at ambient temperature and the mixture is refluxed for 20 hours. By adding pentane a precipitate is obtained which is filtered off, washed twice with 3 ml of ethyl ether and dried under reduced pressure.

Yield 1.25 g (87%).

EXAMPLE 7

Synthesis of the complex cis-RuCl$_2$[(2S,4S)-(−)-(2, 4-bis-(diphenylphosphine)pentane][2-(H$_2$NCH$_2$) C$_5$H$_4$N](12)

The complex cis-RuCl$_2$(PPh$_3$)$_2$[2-(H$_2$NCH$_2$)C$_5$H$_4$N] (5) (303 mg, 0.377 mmol) and (S,S)-(−)-Skewphos (166 mg, 0.377 mmol) were suspended in 5 ml toluene. The mixture is refluxed for 20 hours; the solution volume is then reduced to one half and the complex is precipitated by adding 2 ml of pentane. The solid obtained is filtered off, and dried under reduced pressure.

Yield: 200 mg (74%). Elemental analysis (%) calculated for C$_{35}$H$_{38}$Cl$_2$N$_2$P$_2$Ru: C, 58.34; H, 5.32; N, 3.89; found: C, 58.06; H, 5.17; N, 3.63. $^1$H NMR (200.1 MHz, CDCl$_3$, 20° C., TMS): δ 8.78 (d, J(HH)=3.1 Hz, 1H; ortho-C$_5$H$_4$N), 7.95-6.69 (m, 23H; aromatic protons), 4.20 (wide s, 1H; NH), 3.61 (d, J(HH)=15.6 Hz, 1H; CHN), 3.37 (m, 1H; PCH), 3.07 (m, 1H; PCH), 2.81 (wide s, 1H; CHN), 2.33-1.63 (m, 2H; CH$_2$), 1.25 (wide s, 1H; NH), 1.16 (dd, J(HP), J(HH)=7.2, 13.6 Hz, 3H; CH$_3$), 0.76 (dd, J(HP), J(HH)=7.0, 11.6, 3H; CH$_3$). $^{13}$C{$^1$H} NMR (50.3 MHz, CDCl$_3$, 20° C., TMS): δ 158.4 (s, NCCH$_2$), 149.6 (s, NCH), 139.8-119.3 (m, aromatic C), 51.5 (s, CH$_2$N), 37.8 (s; CH$_2$), 33.5 (d, J(CP)=27.2 Hz; CHP), 20.3 (d, J(CP)=32.1 Hz; CHP), 18.9 (d, J(CP)=6.6 Hz; CH$_3$), 17.7 (d, J(CP)=1.6 Hz; CH$_3$). $^{31}$P{$^1$H} NMR (81.0 MHz, CDCl$_3$, 20° C., H$_3$PO$_4$): δ 64.8 (d, J(PP)=44.7 Hz), 45.3 (d, J(PP)=44.7 Hz).

EXAMPLE 8

Synthesis of the complex cis-RuCl$_2${(R)-(−)-1-[(S)-2-(diphenylphosphino)ferrocenyl]ethyldicyclohexylphosphine}[2-(H$_2$NCH$_2$)C$_5$H$_4$N] (14)

The complex RuCl$_2$(PPh$_3$)$_3$ (1) (228 mg, 0.238 mmol) and the phosphine (R)—(S)-(−)-Josiphos (141 mg, 0.237 mmol) were suspended in 10 ml of toluene and refluxed for 30 minutes. 2-(aminomethyl)pyridine (26 µL, 0.252 mmol) was added to the reaction mixture, having been brought to ambient temperature. The mixture was again heated under reflux (110° C.) for 4 hours. The compound was then precipitated with pentane, filtered off, washed twice with 3 ml ethyl ether and the solid was dried under reduced pressure.

Yield: 182 mg (88%). Elemental analysis (%) calculated for C$_{42}$H$_{52}$Cl$_2$N$_2$P$_2$RuFe: C, 57.68; H, 5.99; N, 3.20; found: C, 57.47; H, 5.80; N, 3.25. $^1$H NMR (200.1 MHz, CDCl$_3$, 20° C., TMS): δ 10.25 (s, 1H; o-H-pyridine), 8.39-7.15 (m, 13H; aromatic protons), 5.10 (m, 1H; CHCH$_3$), 4.47 (m, 1H; C$_5$H$_3$), 4.30 (m, 1H; C$_5$H$_3$), 3.84-3.34 (m, 5H; C$_5$H$_3$, CH$_2$NH$_2$) 3.66 (s, 5H; C$_5$H$_5$), 2.20-0.52 (m, 25H; CH$_3$Cy). $^{31}$P{$^1$H} NMR (81.0 MHz, CDCl$_3$, 20° C., H$_3$PO$_4$): δ 60.8 (d, J(PP)=40.9 Hz), 39.7 (d, J(PP)=40.9 Hz).

B. Catalytic Tests

The ruthenium(II) complexes of the present invention can be used for preparing alcohols from the corresponding ketones, by means of hydrogen transfer reactions. In presence of the new ruthenium based catalysts and of an alkali metal hydroxide, cyclic ketones, linear dialkylketones, alkylarylketones and diarylketones R$^6$C(=O)R$^7$ where R$^6$ and R$^7$ represent a saturated or unsaturated aliphatic group, or an aromatic hydrocarbon group, which can have or not have alkyl substituent groups, substituent groups containing oxygen, halogen atoms, or a heterocyclic group, can be reduced to alcohols.

The reduction reactions are conducted in 2-propanol under reflux with a substrate/catalyst ratio between 1000 and 10000 and in the presence of an alkali metal hydroxide at 2 mol % relative to the substrate. In table 1 by way of example the conversion value of various substrates are given. It should be noted that the acetone that forms by oxidation of the 2-propanol can be separated from the reaction mixture, by exploiting its lower boiling point relative to 2-propanol. By way of example, catalytic tests conducted at 30° C. under hydrogen atmosphere at low pressure (2-3 atm) are also given, from which it is seen that under such conditions, there is complete conversion of ketone to alcohol, thus demonstrating that these complexes are also active in hydrogenation reactions with molecular hydrogen.

B1. Catalytic Tests with Non Chiral Catalysts

All the procedures were conducted under argon atmosphere, using previously de-aerated 2-propanol.

EXAMPLE 9

Catalytic Reduction of Acetophenone in the Presence of Ruthenium(II) Complexes

The process of acetophenone reduction catalysed by the complex (10) is described. The same method was used with the complexes (3-9), the results being shown in table 1.

a) Reduction of Acetophenone Catalysed by the Complex (10)

The catalyst solution is prepared in a 10 ml Schlenk by adding 5 ml of 2-propanol to the complex (10) (3.5 mg, 0.005 mmol). By stirring, the complex dissolves completely within a few minutes. In a second 50 ml Schlenk 1 ml of the previously prepared solution containing the catalyst and 0.5 ml of a 0.1 M NaOH solution in 2-propanol are added to a solution of acetophenone (240 µL, 2 mmol) in 19 ml of 2-propanol under reflux. The start of the reaction is considered to be when the complex is added. The molar ratios of acetophenone/catalyst/NaOH are 2000/1/50.

b) Reduction of Acetophenone Catalysed by the Complex (10) Prepared In Situ

The catalyst solution is prepared in situ in a 10 ml Schlenk by adding 1.0 µl of 2-(H$_2$NCH$_2$)C$_5$H$_4$N (0.01 mmol) and 5 ml of 2-propanol to the complex (2) (4.3 mg, 0.005 mmol). By stirring, the complex dissolves completely within a few minutes.

Separately, in a second 50 ml Schlenk, 1 ml of the previously prepared solution containing the catalyst and 0.5 ml of a 0.1 M NaOH solution in 2-propanol are added to a solution of acetophenone (240 µl, 2 mmol) in 19 ml of 2-propanol under reflux. The start of the reaction is considered to be when the complex is added. The molar ratios of acetophenone/catalyst/NaOH are 2000/1/50 (table 1).

TABLE 1

Catalytic reduction of acetophenone to 1-phenylethanol in the presence of ruthenium complexes

| Complex | Molar ratio Acetophenone/ Ru/NaOH | Conversion % (min) | TOF (h$^{-1}$) |
|---|---|---|---|
| 3 | 2000/1/50 | 83 (90) | 2400 |
| 4 | 2000/1/40 | 97 (10) | 28000 |
| 5 | 2000/1/50 | 98 (74) | 5200 |
| 6 | 2000/1/40 | 92 (30) | 11000 |
| 7 | 2000/1/50 | 98 (10) | 34700 |
| 7 | 5000/1/125 | 96 (10) | 90000 |
| 8 | 2000/1/50 | 1 (30) | 32 |
| 9 | 2000/1/50 | 97 (1) | 220000 |
| 9 | 5000/1/125 | 83 (33) | 71600 |
| 9 | 10000/1/250 | 95 (90) | 12000 |
| 9[a] | 2000/1/20 | 94 (10) | 54400 |
| 10 | 2000/1/50 | 97 (1) | 300000 |
| 10 | 5000/1/125 | 85 (5) | 220000 |
| 10 | 10000/1/250 | 97 (35) | 180800 |
| 10[a] | 2000/1/20 | 97 (10) | 126400 |
| 10[a] | 5000/1/50 | 81 (150) | 60000 |
| formation reaction of (10) in situ | | | |
| 2/2-(H$_2$NCH$_2$)C$_5$H$_4$N (1:2) | 2000/1/50 | 96 (0.5) | 250000 |

[a]base: K$_2$CO$_3$

EXAMPLE 10

Catalytic Reduction of Linear and Cyclic Dialkyl Ketones, Alkylaryl Ketones and Diarylketones in the Presence of the Complex (10)

The catalyst solution is prepared in a 10 ml Schlenk by adding 5 ml of 2-propanol to the complex (10) (3.5 mg, 0.005 mmol). By stirring the complex dissolves completely over a period of a few minutes.

Separately, in a second 50 ml Schlenk, 1 ml of the previously prepared solution containing the catalyst and 0.5 ml of a 0.1 M NaOH solution in 2-propanol are added to a 2 mmol solution of ketone in 19 ml of 2-propanol under reflux. The start of the reaction is considered to be when the complex is added. The molar ratios of ketone/catalyst/NaOH are 2000/1/50. The gas chromatographic analysis data are given in table 2.

TABLE 2

Catalytic reduction of ketones to alcohols in the presence of the complex (10). The molar ratios of ketone/complex/NaOH are equal to 2000/1/50/

| Ketone | % Conversion (min) | TOF (h$^{-1}$) |
|---|---|---|
| Acetophenone | 97 (1) | 300000 |
| 5-hexen-2-one | 98 (36) | 280800 |
| Cyclopentanone | 97 (5) | 87300 |
| Cyclohexanone | 99 (30 sec) | 413000 |
| Benzophenone | 98 (10) | 80000 |

The experimental results show that with the complex (10), reduction of linear and cyclic alkyl ketones and aryl ketones to the corresponding alcohols in 2-propanol under reflux is very fast and is complete within a few minutes, with substrate/catalyst ratios between 2000-5000 (see text). The turnover frequency (TOF) values are between 80000 and 413000 h$^{-1}$, depending on the steric and electronic characteristics of the substrate (table 2). Examination of the data in the literature indicates that complex (10) is one of the most active hydrogen transfer catalysts, because the previously reported systems have exhibited a TOF for acetophenone of generally less than 10000 h$^{-1}$ except for the Mathieu complex which exhibits a TOF of 90000 h$^{-1}$ (H. Yang, M. Alvarez, N. Lugan, R. Mathieu, *J. Chem. Soc., Chem. Commun.* 1995, 1721).

By way of example the synthesis of benzhydrol, an important intermediate for preparing antihistamines and other pharmaceutical derivatives from benzophenone, is given hereinafter. The reaction can also be conducted starting from a more concentrated solution of acetophenone (1 M) and removing the acetone produced by distillation.

EXAMPLE 11

Benzhydrol Synthesis 1.8 g of benzophenone (10 mmol) and 45 ml of 2-propanol are introduced into a 100 ml flask under argon atmosphere. The system is heated under reflux. 2.5 ml of a 0.1 M solution of NaOH in 2-propanol and 2 ml of a 2-propanol solution containing the catalyst (10) (1.8 mg, 0.0025 mmol) are added. The molar ratios of benzophenone/catalyst/NaOH are equal to 4000/1/100. $^1$H NMR analysis of the mixture shows that the reaction is complete after 30 minutes. By evaporating the solvent, a colourless residue is obtained which is extracted with 30 ml of diethyl ether. This solution is then passed through a silica filled column to remove the catalyst and sodium hydroxide. The filtrate is dried by adding Na$_2$SO$_4$ and, after filtering and removal of the solvent, the benzhydrol is recovered and then dried under reduced pressure (10$^{-2}$ mmHg).

Product isolated: 1.62 g (yield: 88%).

Using the new catalysts (3-10) in the presence of 2-propanol as hydrogen source therefore this procedure represents a valid alternative, and of wide applicative interest, to the use of stoichiometric reducers or molecular, hydrogen for the small and medium scale synthesis of alcohol. The use of the catalysts (3-10) involves a high rate of reduction of the ketones with quantitative conversion into the products within a few minutes and therefore these ruthenium complexes are ideal for the synthesis of an extensive number of alcohols of R$_2$CHOH type and of racemic mixtures of RR'CHOH where the R, R' groups are saturated or unsaturated linear or cyclic aliphatic groups, or aromatic hydrocarbon groups, which may either possess or not possess substituent alkyl groups, or substituent groups containing oxygen, halogen or pyridine atoms. The high chemical selectivity and the ease of isolating the alcohols produced renders this catalytic process an alternative method to the use of classical reducing agents such as NaBH$_4$, LiAlH$_4$ (J. March, *Advanced Organic Chemistry*, John Wiley, New York (USA), 1984, p. 809) and Al(OC$_3$H$_7$)$_3$ (Meerwein-Ponndorf-Verley reaction) (H. Meerwein, R. Schmidt, Liebigs *Ann. Chem.* 1925, 444, 221; A. Verley, *Bull Soc. Fr.* 1925, 37, 537; W Ponndorf, *Angew. Chem.* 1926, 39, 138; A. L. Wilds, *Org. React.* 1944, 2, 178) which are extensively used in industry.

B2. Catalytic Tests with Chiral Catalysts

All the processes were conducted under argon or hydrogen atmosphere, using previously de-aerated 2-propanol.

EXAMPLE 12

Enantioselective Reduction of Acetophenone (0.1 M) in the Presence of Chiral Complexes of Ruthenium A procedure for the enantioselective reduction of acetophenone catalysed by the complex (12) is described. The same method was used with the complexes (11-15), the results being shown in table 3, while in table 4 the results of the reactions conducted under argon or hydrogen atmosphere by means of the complex (12) are given.

a). Enantioselective Reduction of Acetophenone to 1-Phenylethanol Catalysed by the Complex (12)

The chiral catalyst (12) (3.6 mg, 0.005 mmol) is suspended in 3 ml of 2-propanol in a 10 ml Schlenk, and 2 ml of a 0.1 M NaOH solution in 2-propanol are added, with consequent dissolution of the product.

Separately, in a 50 ml Schlenk, acetophenone (240 μl, 2 mmol) is dissolved in 19 ml of de-aerated 2-propanol. The system is heated under reflux and 1 ml of the solution containing the previously prepared catalyst is added. The molar ratios of acetophenone/catalyst/NaOH are 2000/1/40. The start of the reaction is considered to be when the complex is added. The results obtained from the gas chromatographic analysis are given in table 3.

TABLE 3

Enantioselective reduction of acetophenone to 1-phenylethanol in the presence of chiral complexes of ruthenium

| Complex | Acetophenone/Ru/NaOH | % Conv. (min) | ee % | TOF (h$^{-1}$) |
|---|---|---|---|---|
| 11 | 3000/1/28 | 97 (10) | 1 S | 20000 |
| 12 | 2000/1/40 | 96 (1) | 84 S | 300000 |
| 12 | 5000/1/100 | 96 (2) | 82 S | 180000 |
| 12 | 10000/1/200 | 95 (5) | 84 S | 252000 |
| 12[a] | 2000/1/40 | 95 (45) | 90 S | 3000 |
| 12[b] | 2000/1/10 | 94 (10) | 81 S | 25000 |
| 12[c] | 2000/1/40 | 94 (90) | 90 S | 2500 |
| 13 | 100/1/3 | 98 (5) | 23 S | 2000 |

TABLE 3-continued

Enantioselective reduction of acetophenone to 1-phenylethanol in the presence of chiral complexes of ruthenium

| Complex | Acetophenone/Ru/NaOH | % Conv. (min) | ee % | TOF (h$^{-1}$) |
|---|---|---|---|---|
| 13 | 200/1/1 | 95 (5) | 59 S | 34000 |
| 14 | 2000/1/40 | 97 (2) | 82 R | 225000 |
| 14[a] | 2000/1/40 | 95 (120) | 92 R | 3000 |
| 15 | 2000/1/40 | 97 (5) | 44 R | 84000 |
| 15[a] | 2000/1/40 | 63 (130) | 49 R | 1700 |

The reaction was conducted at:
[a]40° C.;
[b]70° C.;
[c]40° C.,
base: K$_2$CO$_3$

TABLE 4

Enantioselective reduction of acetophenone to 1-phenylethanol in the presence of the complex (12) at 30° C. under Ar or hydrogen atmosphere.

| Atmosphere | Ketone (M) | Ketone/Ru/NaOH | Conv. % (min) | ee % | TOF (h$^{-1}$) |
|---|---|---|---|---|---|
| Ar | 0.1 | 2000/1/40 | 91 (2 h) | 91 S | 1700 |
| H$_2$ (3 atm) | 0.1 | 2000/1/40 | 96 (2 h) | 86 S | 2200 |
| Ar | 1 | 2000/1/40 | 75 (17 h) | 71 S | 570 |
| H$_2$ (3 atm) | 1 | 2000/1/40 | 100 (17 h) | 39 S | 1320 |

EXAMPLE 13

Enantioselective Reduction of Ketones, Catalysed by the Chiral Complex (12)

The chiral catalyst (12) (3.6 mg, 0.005 mmol) is suspended in 3 ml of 2-propanol in a 10 ml Schlenk, and 2 ml of a 0.1 M NaOH solution in 2-propanol are added, with consequent dissolution of the product.

Separately, in a 50 ml Schlenk the ketone (2 mmol) is dissolved in 19 ml of de-aerated 2-propanol. The system is heated under reflux and 1 ml of the solution containing the previously prepared catalyst is added.

The molar ratios of acetophenone/catalyst/NaOH are 2000/11/40. The results obtained from the gas chromatographic analysis are given in table 5.

TABLE 5

Enantioselective reduction of ketones to alcohols catalysed by the complex (12). The molar ratios of substrate/catalyst/base are equal to 2000/1/40.

| Ketone | Alcohol | % Conversion (min) | ee % | TOF (h$^{-1}$) |
|---|---|---|---|---|
| Acetophenone | 1-phenylethanol | 96 (1) | 84 S | 300000 |
| 2-chloroacetophenone | 2'-chloro-1-phenylethanol | 96 (1) | 89 S | 293000 |
| 2-methoxyacetophenone | 2'-methoxy-1-phenylethanol | 96 (2) | 94 S | 245000 |
| 5-hexen-2-one | 5-hexen-2-ole | 98 (5) | 24 S | 81000 |
| 4-chlorobenzophenone | 4-chlorobenzhydrol | 98 (6) | 0 | 140000 |
| 2-benzoylpyridine | phenyl(2-pyridyl)methanol | 98 (5) | 90 S | 150000 |

EXAMPLE 14

Synthesis of (S)-2'-chloro-phenylethanol 46 ml of de-aerated 2-propanol are introduced into a 100 ml flask under argon atmosphere and 1.3 ml of 2-chloroacetophenone (10 mmol) are added, the system then being heated under reflux. Separately, in a 10 ml Schlenk, the catalyst (12) (2.1 mg, 0.003 mmol) is dissolved in 3 ml of a 0.1 M NaOH solution in 2-propanol. The complex dissolves rapidly and after about a minute 2 ml of this solution are introduced into the reaction flask. The molar ratios of 2-chloroacetophenone/catalyst/NaOH are equal to 5000/1/100. The reaction is checked by means of gas chromatographic analysis at 15 and 30 minutes. After one hour under reflux, $^1$H NMR analysis shows complete conversion of the ketone to alcohol. By evaporating the solvent, an oil is obtained to which 20 ml of ethyl ether are added and the solution is filtered through a silica filled column to remove the catalyst and the NaOH base. The solution is dried over $Na_2SO_4$ and the filtrate is placed in a previously weighed small flask. After removal of the ether at ambient temperature under reduced pressure, the oily product was re-heated to 110° C. for about 2 hours to remove traces of 2-propanol. 1.28 g (84% yield) of alcohol of S configuration (91% ee) were obtained.

EXAMPLE 15

Synthesis of (S)-2'-methoxy-1-phenylethanol

Using the same procedure as was used for (S) 2'-chloro-1-phenylethanol, synthesis of (S)-2'-methoxy-1-phenylethanol was undertaken starting from 2-methoxyacetophenone. The molar ratios used for ketone/(12)/base are equal to 5000/1/100. Starting from 1.4 ml (10 mmol) of 2-methoxyacetophenone, 1.24 g of alcohol (80% yield) of S configuration (94% ee) were obtained.

The invention claimed is:

1. A Ruthenium(II) complex of general formula (I)

[RuXYL$_m$L']       (I)

wherein:
X, Y, L, L' can be:
X, Y equal or different and be a halogen or a hydrogen;
L ligands chosen from the groups consisting of
a) a monodentate phosphine of general formula PR$^1$R$^2$R$^3$ where R$^1$, R$^2$ and R$^3$ can be equal or different and be aliphatic or aromatic groups,
b) a bidentate phosphine of general formula PR'$_2$(CH$_2$)$_x$PR"$_2$ with x equal to 2, 3 or 4 where R' and R" can be equal or different and be aliphatic or aromatic groups,
c) an optically active diphosphine,
and m can be equal to 1 or 2 with the proviso that m is equal to 1 when the ligand L is chosen from group b) or c) and equal to 2 when the ligand L is chosen from group a) and that in this case the ligands L can be equal or different;
L' is a bidentate ligand of 2-(aminomethyl)pyridine type of formula (II)

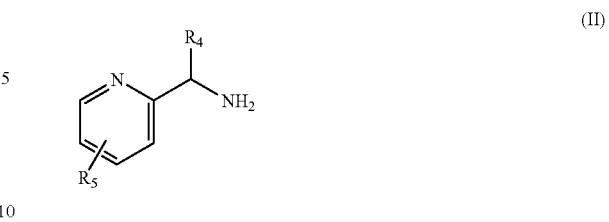

where R$^4$, R$^5$ can be equal or different and can be H, aliphatic or aromatic groups.

2. A Ruthenium(II) complex as claimed in claim 1 wherein the ligands X and Y can be trans or cis.

3. A Ruthenium(II) complex as claimed in claim 1 of formula (III)

[RuXYL$_2$L']       (III)

wherein:
X, Y independently are a halogen or a hydrogen;
L are monodentate phosphines, equal or different, chosen from group a);
L' is a bidentate ligand of 2-(aminomethyl)pyridine type of formula (II).

4. A Ruthenium(II) complex as claimed in claim 3 wherein X, Y can be trans or cis.

5. A Ruthenium(II) complex as claimed in claim 3 wherein X and Y can be independently a chlorine or a hydrogen, L can be the monodentate phosphine PPh$_3$ and L' can be 2-(aminomethyl)pyridine.

6. A Ruthenium(II) complex as claimed in claim 1 of formula (IV)

[RuXYL$_1$L']       (IV)

wherein:
X, Y independently are a halogen or a hydrogen;
L is a bidentate phosphine chosen from group b) or an optically active diphosphine chosen from group c);
L' is a bidentate ligand of 2-(aminomethyl)pyridine type of formula (II).

7. A Ruthenium(II) complex as claimed in claim 6 wherein X, Y can be trans or cis.

8. A Ruthenium(II) complex as claimed in claim 6 wherein X and Y can be a chlorine, L is a diphosphine chosen from the group consisting of PPh$_2$(CH$_2$)$_2$PPh$_2$, PPh$_2$(CH$_2$)$_3$PPh$_2$, PPh$_2$(CH$_2$)$_4$PPh$_2$ and L' is 2-(aminomethyl) pyridine.

9. A Ruthenium(II) complex as claimed in claim 6 wherein X and Y can be a chlorine and L is an optically active diphosphine chosen from the group consisting of (2S,3S)-(-)-2,3-bis-(diphenylphosphino)butane (CHIRAPHOS), (S)-(-)-2,2'-bis-(di-p-tolylphosphino)-1,1'-binaphthyl (Tol-BINAP), (2S,4S)-(-)-2,4-bis-(diphenylphosphino)pentane (SKEWPHOS), (4R,5R)-(-)-O-isopropylidene-2,3-dihydroxo-1,4-bis(diphenylphosphino)butane (DIOP), (R)-(-)-1-[(S)-2-(diphenylphosphino)ferrocenyl]ethyldicyclohexylphosphine (JOSIPHOS) and L' is 2-(aminomethyl)pyridine.

10. A Ruthenium(II) complex of general formula (I)

[RuXYL$_m$L']       (I)

wherein:
X, Y, L, L' can be:
X, Y equal or different and be a halogen or a hydrogen;
L ligands chosen from the groups consisting of
a) a monodentate phosphine of general formula PR$^1$R$^2$R$^3$ where R$^1$, R$^2$ and R$^3$ can be equal or different and can be aliphatic or aromatic groups, b) a bidentate phosphine of general formula PR'$_2$(CH$_2$)$_x$PR"$_2$ with x equal to 2, 3 or 4 where R' and R"can be equal or different and be aliphatic or aromatic groups, c) an optically active diphosphine, and m can be equal to 1 or 2 with the proviso that m is equal to 1 when the ligand L is chosen from group b) or c) and equal to 2 when the ligand L is chosen from group a) and that in this case the ligands L can be equal or different;

L' is a bidentate ligand of 2-(aminomethyl)pyridine type of formula (II)

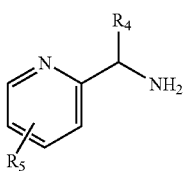
(II)

where R$^4$, R$^5$ can be equal or different and can be H, aliphatic or aromatic groups obtainable in situ by a synthesis process wherein RuCl$_2$(PPh$_3$)$_3$ or RuCl$_2$[PPh$_2$(CH$_2$)$_4$PPh$_2$](PPh$_3$) is used as a starting reagent and said reagent is treated with 2-(aminomethyl)pyridine and optionally treated with a suitable phosphine.

11. A method for reduction of a ketone to prepare an alcohol comprising the steps of:

providing a ruthenium(II) complex of general formula (I)

[RuXYL$_m$L'] (I)

wherein:

X, Y, L, L' can be:

X, Y equal or different and be a halogen or a hydrogen;

L ligands chosen from the groups consisting of:

a) a monodentate phosphine of general formula PR$^1$R$^2$R$^3$ where R$^1$, R$^2$ and R$^3$ can be equal or different and be aliphatic or aromatic groups, b) a bidentate phosphine of general formula PR'$_2$(CH$_2$)$_x$PR"$^2$ with x equal to 2, 3 or 4 where R' and R" can be equal or different and be aliphatic or aromatic groups, c) an optically active diphosphine, and m can be equal to 1 or 2 with the proviso that m is equal to 1 when the ligand L is chosen from group b) or c) and equal to 2 when the ligand L is chosen from group a) and that in this case the ligands L can be equal or different;

L' is a bidentate ligand of 2-(aminomethyl)pyridine type of formula (II)

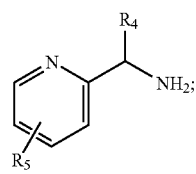
(II)

where R$^4$, R$^5$ can be equal or different and can be H, aliphatic or aromatic groups; and reducing a ketone to an alcohol corresponding to the ketone, in an enantioselective reduction reaction or a non enantioselective reduction reaction, by transferring hydrogen from another alcohol to the ketone, wherein said ruthenium (II) complex is used as a catalyst in the reduction reaction.

12. A method for reduction of a ketone to prepare an alcohol comprising the steps of:

providing a ruthenium(II) complex of general formula (I)

[RuXYL$_m$L'] (I)

wherein:

X, Y, L, L' can be:

X, Y equal or different and be a halogen or a hydrogen;

L ligands chosen from the groups consisting of a) a monodentate phosphine of general formula PR$^1$R$^2$R$^3$ where R$^1$, R$^2$ and R$^3$ can be equal or different and be aliphatic or aromatic groups, b) a bidentate phosphine of general formula PR'$_2$(CH$_2$)$_x$PR"$_2$ with x equal to 2, 3 or 4 where R' and R" can be equal or different and be aliphatic or aromatic groups, c) an optically active diphosphine, and m can be equal to 1 or 2 with the proviso that m is equal to 1 when the ligand L is chosen from group b) or c) and equal to 2 when the ligand L is chosen from group a) and that in this case the ligands L can be equal or different;

L' is a bidentate ligand of 2-(aminomethyl)pyridine type of formula (II)

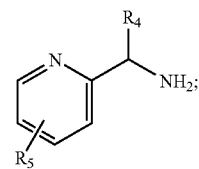
(II)

where R$^4$, R$^5$ can be equal or different and can be H, aliphatic or aromatic groups; and reducing a ketone to an alcohol corresponding to the ketone, in an enantioselective reduction reaction or a non enantioselective reduction reaction, by reacting the ketone with gaseous hydrogen, wherein said ruthenium (II) complex is used as a catalyst in the reduction reaction.

13. A method for reduction of a ketone to prepare an alcohol comprising the steps of:

providing a ruthenium(II) complex of general formula (I)

[RuXYL$_m$L'] (I)

wherein:

X, Y, L, L' can be:

X, Y equal or different and be a halogen or a hydrogen;

L ligands chosen from the groups consisting of a) a monodentate phosphine of general formula PR$^1$R$^2$R$^3$ where R$^1$, R$^2$ and R$^3$ can be equal or different and be aliphatic or aromatic groups, b) a bidentate phosphine of general formula PR'$_2$(CH$_2$)$_x$PR"$_2$ with x equal to 2, 3 or 4 where R' and R" can be equal or different and be aliphatic or aromatic groups, c) an optically active diphosphine, and m can be equal to 1 or 2 with the proviso that m is equal to 1 when the ligand L is chosen from group b) or c) and equal to 2 when the ligand L is chosen from group a) and that in this case the ligands L can be equal or different;

L' is a bidentate ligand of 2-(aminomethyl)pyridine type of formula (II)

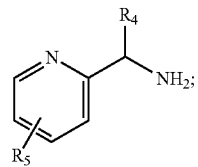

where $R^4$, $R^5$ can be equal or different and can be H, aliphatic or aromatic groups; and reducing a ketone to an alcohol corresponding to the ketone, in an enantioselective reduction reaction or a non enantioselective reduction reaction, by a combination of transferring hydrogen from another alcohol to the ketone and by reacting the ketone with gaseous hydrogen, wherein said ruthenium (II) complex is used as a catalyst in the reduction reaction.

14. A process for synthesis of a ruthenium(II) complex as claimed in claim 1 wherein $RuCl_2(PPh_3)_3$ or $RuCl_2[PPh_2(CH_2)_4PPh_2](PPh_3)$ is used as a starting reagent and said reagent is treated with 2-(aminomethyl)pyridine and optionally treated with a suitable phosphine.

15. A process for the in situ synthesis of a ruthenium(II) complex as claimed in claim 1 wherein $RuCl_2(PPh_3)_3$ or $RuCl_2[PPh_2(CH_2)_4PPh_2](PPh_3)$ is used as a starting reagent and said reagent is treated with 2-(aminomethyl)pyridine and optionally treated with a suitable phosphine.

\* \* \* \* \*

UNITED STATES PATENT AND TRADEMARK OFFICE
CERTIFICATE OF CORRECTION

PATENT NO. : 7,638,628 B2  Page 1 of 1
APPLICATION NO. : 11/579371
DATED : December 29, 2009
INVENTOR(S) : Baratta et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 504 days.

Signed and Sealed this

Ninth Day of November, 2010

David J. Kappos
*Director of the United States Patent and Trademark Office*